(12) United States Patent
Kraiter et al.

(10) Patent No.: US 11,076,802 B2
(45) Date of Patent: Aug. 3, 2021

(54) REMOTE ASSESSMENT OF NEUROSTIMULATION

(71) Applicant: BIOTRONIK SE & CO. KG, Berlin (DE)

(72) Inventors: Lauren Kraiter, Tigard, OR (US);
Dirk Muessig, West Linn, OR (US);
Larry Stotts, Tigard, OR (US);
Andreas Becker, Wilsonville, OR (US)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 17/070,225

(22) Filed: Oct. 14, 2020

(65) Prior Publication Data

US 2021/0077017 A1 Mar. 18, 2021

Related U.S. Application Data

(63) Continuation of application No. PCT/EP2019/058144, filed on Apr. 1, 2019.
(Continued)

(51) Int. Cl.
*A61B 5/00* (2006.01)
*A61B 5/16* (2006.01)
(Continued)

(52) U.S. Cl.
CPC .......... *A61B 5/4848* (2013.01); *A61B 5/0022* (2013.01); *A61B 5/0077* (2013.01);
(Continued)

(58) Field of Classification Search
USPC .................................................. 600/300, 301
See application file for complete search history.

(56) References Cited

U.S. PATENT DOCUMENTS 7,819,909 B2 10/2010 Goetz et al.
8,380,314 B2 2/2013 Panken et al.
(Continued)

FOREIGN PATENT DOCUMENTS

WO WO 2016/025989 A1 2/2016

OTHER PUBLICATIONS

Poh, Ming-Zher, and Yukkee C. Poh. "Validation of a standalone smartphone application for measuring heart rate using imaging photoplethysmography." *Telemedicine and e-Health* 23.8 (2017): 678-683.
(Continued)

*Primary Examiner* — Nicole F Lavert
*Assistant Examiner* — Nicole F. Johnson
(74) *Attorney, Agent, or Firm* — Frost Brown Todd LLC

(57) ABSTRACT

The present disclosure relates to a system (1) for remote assessment of a patient (P1), comprising: a first device (2) associated to a physician (P2), a second device (3) associated to the patient (P1), a medical device (4) associated to the patient (P1), wherein the second device (3) is configured to communicate with the medical device (4), and wherein the medical device (4) is configured to be programmed via the second device (3), wherein the first device (2) is further configured to communicate with the second device (3), and wherein the second device (3) is configured to be controlled via the first device (2), and wherein the second device (3) is configured to acquire data (S1, S2) indicative of at least one physiological parameter or of several physiological parameters (HR, F, P) of the patient (P1). Furthermore, a method for remote assessment is provided.

15 Claims, 3 Drawing Sheets

Related U.S. Application Data

(60) Provisional application No. 62/657,964, filed on Apr. 16, 2018, provisional application No. 62/713,587, filed on Aug. 2, 2018.

(51) Int. Cl.
*A61B 5/08* (2006.01)
*A61B 5/11* (2006.01)
*A61N 1/36* (2006.01)
*A61N 1/372* (2006.01)
*G10L 15/08* (2006.01)

(52) U.S. Cl.
CPC .......... *A61B 5/0816* (2013.01); *A61B 5/1116* (2013.01); *A61B 5/163* (2017.08); *A61B 5/165* (2013.01); *A61B 5/4266* (2013.01); *A61B 5/442* (2013.01); *A61B 5/4803* (2013.01); *A61B 5/4824* (2013.01); *A61N 1/36071* (2013.01); *A61N 1/37282* (2013.01); *G10L 15/08* (2013.01)

(56) References Cited

U.S. PATENT DOCUMENTS

| 8,694,115 | B2 | 4/2014 | Goetz et al. |
| 9,278,208 | B1 | 3/2016 | Gilson et al. |
| 9,414,776 | B2 | 8/2016 | Sillay et al. |
| 2011/0082520 | A1 | 4/2011 | McElveen, Jr. |
| 2012/0190936 | A1 | 7/2012 | Rao et al. |
| 2014/0276549 | A1 | 9/2014 | Osorio |
| 2016/0158553 | A1 | 6/2016 | Panken et al. |
| 2017/0050035 | A1* | 2/2017 | Gupta ............... A61N 1/36021 |

OTHER PUBLICATIONS

International Search Report and Written Opinion dated May 15, 2019 for International Application No. PCT/EP2019/058144, 11 pages.

* cited by examiner

US 11,076,802 B2

REMOTE ASSESSMENT OF NEUROSTIMULATION

CROSS-REFERENCE TO RELATED APPLICATIONS (Not Applicable)

STATEMENT REGARDING FEDERALLY SPONSORED RESEARCH OR DEVELOPMENT (Not Applicable)

THE NAMES OF THE PARTIES TO A JOINT RESEARCH AGREEMENT (Not Applicable)

INCORPORATION-BY-REFERENCE OF MATERIAL SUBMITTED ON A COMPACT DISC OR AS A TEXT FILE VIA THE OFFICE OF ELECTRONIC FILING SYSTEM (EFS-WEB)

(Not Applicable)

STATEMENT REGARDING PRIOR DISCLOSURES BY THE INVENTOR OR A JOINT INVENTOR (Not Applicable)

BACKGROUND OF THE INVENTION

The invention relates to a system for remote assessment of a patient as well as to a corresponding method.

Assessment of different stimulation parameters for pain management is presently limited to qualitative, subjective feedback from the patient. In addition to the lack of objective assessment tools, the management of spinal cord stimulation or other neurostimulation therapies for chronic pain imposes a significant burden on patients, providers, and company representatives due to frequent in-office follow-up adjustments.

Particularly, using video conferencing for remote follow ups is known e.g. from U.S. Pat. No. 7,819,909 B2, U.S. Pat. No. 8,380,314 B2, U.S. Pat. No. 8,694,115 B2, U.S. Pat. No. 9,278,208 B1, U.S. Pat. No. 9,414,776 B2, US 2011/0082520 A1 (now abandoned), US 2012/0190936 A1 (now abandoned), US 2016/0158553 A1 (now U.S. Pat. No. 10,258,798 B2), US 2017/0050035 A1 (now U.S. Pat. No. 10,029,106 B2).

Further, while existing solutions of remote programming of medical devices also address the time and travel burden of in-office follow-ups, they do not improve on the need for objective assessment of stimulation programming e.g. for pain relief.

BRIEF SUMMARY OF THE INVENTION

Thus, based on the above, it is an objective to provide a system and a method for remote assessment of a patient, particularly regarding neurostimulation applied to relieve pain.

A system having the features of claim 1 as well as a method having the features of claim 10 are disclosed. Further embodiments are stated in the corresponding sub claims and are described below.

In one aspect, a system for remote assessment of a patient is disclosed, comprising
a first device associated to a physician,
a second device associated to the patient,
a medical device associated to the patient, wherein the second device is configured to communicate with the medical device (particularly in a wireless fashion), and wherein the medical device is configured to be programmed via the second device,
wherein the first device is further configured to communicate with the second device (particularly in a wireless fashion), and wherein the second device is configured to be temporarily controlled via the first device, and
wherein the second device is configured to acquire data representing at least one physiological parameter or of several physiological parameters of the patient.

The first device may be configured to display at least one of said data, said at least one physiological parameter, said several physiological parameters, or a quantity derived from said data (e.g. to a physician),
wherein the first device and/or the second device and/or the server in communicative connection to the first and the second device and/or the medical device and/or the service center is configured to calculate a score using said at least one parameter or said several parameters, and
wherein a baseline pain score is used as a calibration for reporting all assessed pain levels relative to the baseline pain score.

Particularly, for displaying said data etc., the first device comprises an optical display.

Due to the system according to the present disclosure, particularly results of stimulation of a patient with a medical device, e.g. an implantable medical device for neurostimulation or for stimulation of other organs like the heart, can be quantitatively and objectively assessed while reducing the necessity of in-office follow-ups.

Particularly, according to an embodiment, the respective communication between the first device and the second device corresponds to or comprise a wireless (e.g. radio) communication. Further, according to an embodiment, the communication between the medical device and the second device corresponds to or comprises a wireless (e.g. radio) communication.

Particularly, in the framework of the present disclosure a physician can be an actual physician or any other person/medical personal, particularly clinician, qualified to assess the patient and/or the medical device of the patient.

Particularly, according to an embodiment, the second device associated to the patient is configured to pre-process and/or to transfer the data to the first device. Further, particularly, the first device associated to the physician is configured to instruct the second device to transmit the (e.g. pre-processed) data to the first device associated to the physician.

Furthermore, according to an embodiment, said first device associated to the physician is further configured to be in remote communication with the (e.g. implantable) medical device and is further configured to receive data from the medical device.

Furthermore, according to an embodiment, the system is further capable of remote configuration of the (e.g. implantable) medical device via the first device associated to the physician. Further, according to an embodiment, the first device is further configured to instruct the medical device.

Particularly, instructing the (e.g. implantable) medical device can comprise sending data to the medical device, sending current therapy settings to the medical device, send physiological parameters (stored or real-time) to the medical device, changing therapy settings, starting therapy delivery by the medical device.

Furthermore, instructing the medical device can comprise direct communication between the first device and the medical device and/or indirect communication between the first device and the medical device via the second device associated to the patient.

Particularly, the second device associated to the patient can be formed as a remote control, a mobile phone, particularly a smart phone, a computer, particularly a tablet computer, a laptop computer, or a desktop computer.

Furthermore, the first device associated to the physician can be a programming device, a mobile phone, particularly a smart phone, a computer, particularly a tablet computer, a laptop computer, or a desktop computer.

Furthermore, according to an embodiment of the system said data comprises an optical image or a sequence of optical images of a portion of the patient (i.e. a video of said portion of the patient), wherein the second device associated to the patient comprises or is connected to a camera that is configured to acquire said optical image or said sequence of optical images. In addition or alternatively, said data can comprise an audio signal generated by the patient (e.g. breathing sounds of the patient etc.), wherein the second device associated to the patient comprises or is connected to a microphone that is configured to acquire said audio signal. In addition or alternatively, the video and audio can be provided from a third device which is independent of the second device. The third device can e.g. be another computer with an application for recording and transmission of video and audio portions. According to an embodiment, data representing the video and/or audio signal may be transmitted from the recording device to a service center and/or another device, where data analysis can be performed. The data may also be transmitted to another device via the service center.

In addition to a camera and/or a microphone the second device may also comprise other sensors such as an accelerometer for acquiring said data or a part thereof. Additionally or alternatively, further sensors (e.g. for measuring blood pressure or blood oxygenation) may be connected to the second device e.g. via a line connection or a wireless connection.

The respective recording device (e.g. camera or microphone) can be integrated into the second device. However, the camera or microphone can also be a separate component of the second device, respectively, that is connected to a main component of the second device e.g. via a line connection or a wireless connection.

Further, according to an embodiment, the first device or the second device or the server in communicative connection with the first and the second device and/or the medical device or a combination thereof is configured to analyze said optical image or said sequence of optical images to determine at least one or several of the physiological parameters mentioned above. In an exemplary embodiment, the first device is configured to analyze said optical image or sequence of optical images to determine at least one or several of the following physiological parameters mentioned above: a heart rate of the patient, wherein particularly the first device is configured to determine the heart rate from cyclical fluctuations in the light reflection of the facial skin of the patient. Particularly, this approach for extracting a heart rate has been validated for other applications (cf. e.g. P. M.-Z. a. P. Y. C., "Validation of a Standalone Smartphone Application for Measuring Heart Rate Using Imaging Photoplethysmography," Telemedicine and e-Health, vol. 8, pp. 678-683, August 2017); a perspiration of the patient, wherein particularly the first device is configured to determine said perspiration from cumulative light reflection of the skin of the patient; a degree of eye opening of the patient, wherein particularly the first device is configured to determine said degree of eye opening using a facial recognition algorithm carried out by the first device; a dilation of the pupils of the patient, wherein particularly the first device is configured to determine said dilation of the pupils of the patient using a facial recognition algorithm and/or a pupil tracking algorithm carried out by the first device, respectively; a state of a focus of the eyes of the patient (e.g. whether the focus is steady or wandering), wherein particularly the first device is configured to determine said state using a pupil tracking algorithm carried out by the first device; a posture of the patient, wherein particularly the first device is configured to determine said posture by analyzing changes in a sitting position of the patient relative to a reference body outline that can be calibrated with respect to the patient; a facial expression, particularly a number and/or length of wrinkle lines of the face of the patient or a quantity derived therefrom, wherein particularly the first device is configured to determine said number and/or length using a pattern recognition algorithm carried out by the first device; a breathing rate of the patient. In other equal embodiments the second device or the server in communicative connection to the first and the second device and/or the medical device or a combination thereof the first device included is configured to analyse said optical image or said sequence of optical images to determine at least one or several of said physiological parameters mentioned before.

Further, according to an embodiment, the first device or the second device or the server in communicative connection to the first and the second device and/or the medical device or a combination thereof is configured to analyze said video and/or audio signal to determine at least one or several of the following physiological parameters: a tonality and/or pattern of speech of the patient (e.g. an emotional content in the voice of the patient), wherein particularly the first device or the second device or the server in communicative connection to the first and the second device and/or the medical device or a combination thereof is configured to determine said tonality and/or pattern using a voice analyzing algorithm carrier out by the first device; a breathing rate of the patient.

Furthermore, according to an embodiment, the medical device is an implantable medical device that is configured to be implanted into the patient.

Further, according to an embodiment, the medical device is configured for neurostimulation of the patient (particularly spinal cord stimulation, or deep brain stimulation). According to an embodiment, the medical device is configured for cardiac stimulation of the patient.

Particularly, calculation of the score comprises calculation of a weighted sum. Furthermore, particularly, said score is a measure for a physiological state of the patient, wherein particularly said physiological state is a pain experienced by the patient.

Yet another aspect is related to a method for remote assessment of a patient, which method particularly uses a system according to the present disclosure, wherein data indicative (representing) of at least one physiological parameter or of several physiological parameters of the patient is measured by the first device. At least one of said data, said at least one physiological parameter, said several physiological parameters, or a quantity derived from said data may be displayed (e.g. to a physician) via the first device.

Particularly, according to an embodiment of the method, said data comprises a sequence of optical images of a portion of the patient (i.e. a video of said portion of the patient), and/or an audio signal generated by the patient (see also above).

Further, according to an embodiment of the method, the optical image or the sequence of optical images is analyzed by the first device so as to determine at least one or several of the following physiological parameters: a heart rate of the patient, wherein particularly the first device determines the heart rate from cyclical fluctuations in the light reflection of the facial skin of the patient; a perspiration of the patient, wherein particularly the first device determines said perspiration from cumulative light reflection of the skin of the patient; a degree of eye opening of the patient, wherein particularly the first device determines said degree of eye opening using a facial recognition algorithm carried out by the first device; a dilation of the pupils of the patient, wherein particularly the first device determines said dilation of the pupils of the patient using a facial recognition algorithm and/or a pupil tracking algorithm carried out by the first device, respectively; a state of a focus of the eyes of the patient (e.g. whether the focus is steady or wandering), wherein particularly the first device determines said state using a pupil tracking algorithm carried out by the first device; a posture of the patient, wherein particularly the first device determines said posture by analyzing changes in a sitting position of the patient relative to a reference body outline that can be calibrated with respect to the patient; a facial expression, particularly the number and/or length of wrinkle lines of the face of the patient or a quantity derived therefrom, wherein particularly the first device determines said number and/or length using a pattern recognition algorithm carried out by the first device; a breathing rate of the patient. In other equal embodiments said method is performed by the second device or the server in communicative connection to the first and the second device and/or the medical device or a combination thereof the first device included According to a further embodiment of the method, the audio signal is analyzed by the first device or the second device or the server in communicative connection to the first and the second device and/or the medical device or a combination thereof (and/or the service center) so as to determine at least one or several of the following physiological parameters: a tonality and/or pattern of speech of the patient (e.g. an emotional content in the voice of the patient), wherein particularly the first device or the second device or the server in communicative connection to the first and the second device and/or the medical device or a combination thereof determines said tonality and/or pattern using a voice analyzing algorithm carried out by the first device; a breathing rate of the patient.

Furthermore, according to an embodiment of the method, a score is calculated by means of the first device (and/or by the second device and/or the server in communicative connection to the first and the second device and/or the medical device) using said at least one physiological parameter or said several physiological parameters. Particularly, calculation of the score comprises calculation of a weighted sum. Particularly, said score is a measure for a physiological state of the patient.

Furthermore, according to an embodiment of the method, the acquired data is pre-processed by the second device and transmitted to the first device by the second device.

Furthermore, according to an embodiment of the method, the second device is instructed by the first device to transmit the data to the first device associated to the physician.

Furthermore, according to an embodiment of the method, the (e.g. implantable) medical device is instructed (e.g. by the physician) via the first device to change at least one stimulation parameter (therapy setting) of the medical device, particularly in response to one of: the acquired data, the at least one physiological parameter, said several physiological parameters. The instruction may be alternatively communicated from the first device via the server and/or the second device to the (e.g. implantable) medical device.

However, particularly the actual stimulation/therapy of the patient by means of the medical device is not part of the claimed method according to the present disclosure. Particularly, the method is concerned with collecting data from the patient and particularly also with programming the medical device/adjusting at least one stimulation parameter in response to the data or physiological parameters and/or scores determined therefrom.

The features disclosed in regard with the system can be applied to the method and vice versa.

BRIEF DESCRIPTION OF THE SEVERAL VIEWS OF THE DRAWINGS

Further features and embodiments of the present invention shall be described below with reference to the Figures, wherein.

DETAILED DESCRIPTION OF THE INVENTION

Figure 1:
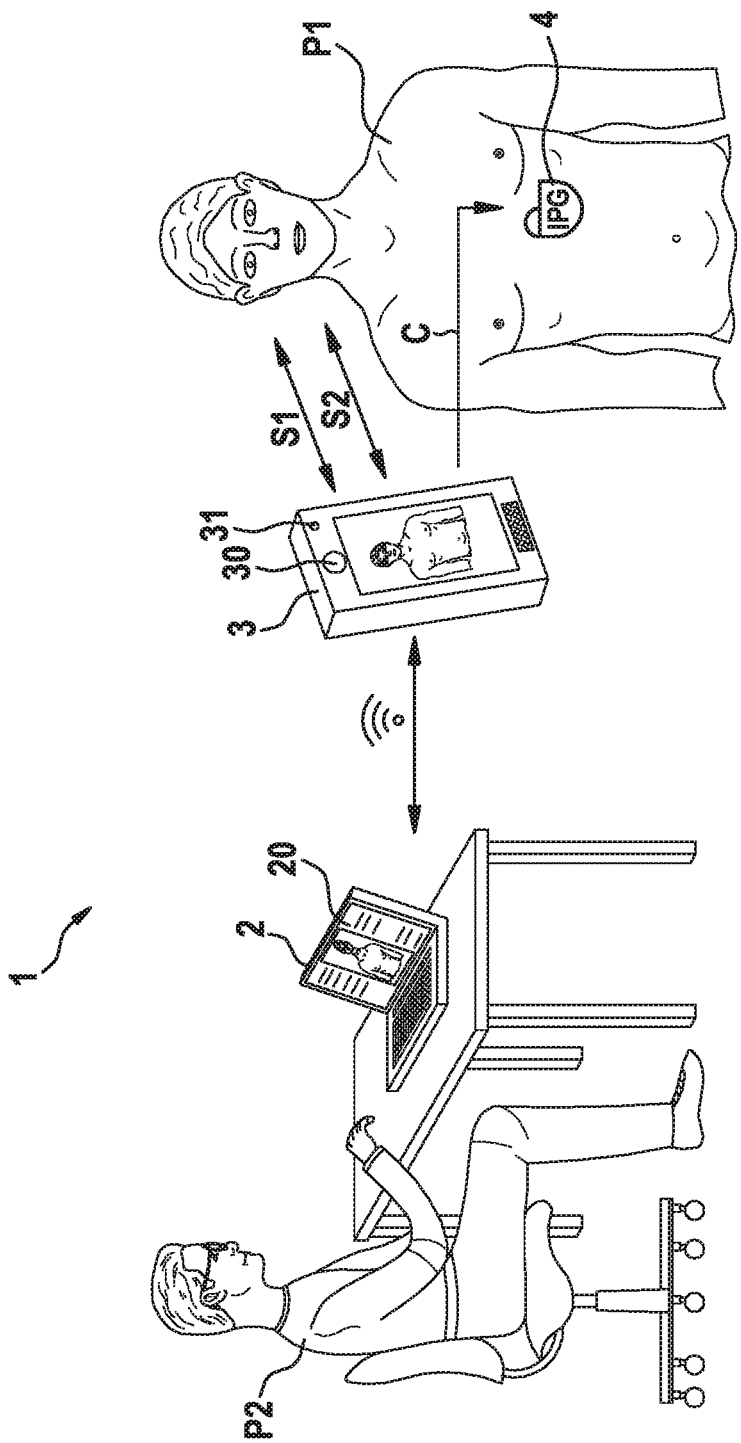
FIG. 1 shows a schematic illustration of an embodiment of a system.

FIG. 1 shows an embodiment of a system 1, particularly, the system 1 comprises a first device 2 associated to a technical user such as a physician P2 or a clinician, a second device 3 associated to a patient P1, a medical device 4 associated to the patient P1, which medical device 4 is particularly implanted into the patient P1, wherein the second device 3 is configured to communicate with the medical device 4, and wherein the medical device 4 is configured to be programmed via the second device 3, wherein the first device 2 is further configured to communicate with the second device 3, and wherein the second device 3 is configured to be controlled via the first device 2, and wherein the second device 3 is configured to acquire data S1, S2 indicative of at least one physiological parameter HR, F, P or of several physiological parameters of the patient P1, and wherein the first device 2 is configured to display (e.g. via a display 20 of the first device 2) at least one of said data S1, S2, said at least one physiological parameter HR, F, P, said several physiological parameters, or a quantity derived from said data S1, S2.

Particularly, the second device 3 (e.g. a patient remote control or another external device) is particularly enabled with a camera 30, and/or a microphone 31, and may also comprise a speaker, as well as a device for accessing the internet in a wireless fashion. The physician/clinician P2 or a designated representative providing follow-up care of the patient's medical device 4 (here e.g. an implantable medical device 4 configured for neurostimulation, particularly spinal cord stimulation) is able to connect to the second device 3 e.g. via a web portal accessed via the first device 2. Optionally, the physician P2 may also be able to initiate direct control of the active stimulation. Whether through direct control or through instruction to the patient P1, the stimulation parameters for the medical device 4 are adjusted; and the video stream S1, i.e. a sequence of optical images S1 generated by the second device 3, is used, particularly supplemented by verbal communication, to assess the present pain level of the patient P1 with each stimulation parameter iteration. Exemplary stimulation parameters are: Choice of electrodes of a multiple electrode lead, stimulation frequency, stimulation pulse width, stimulation amplitude, patterns of stimulation cycling or combinations of stimulation electrodes.

Particularly, the video stream can be analyzed by multiple algorithms in real-time to assess the patient's P1 pain levels. Particularly, the video stream S1 (and/or an audio signal S2) is analyzed for one or more of the following physiological parameters:

- Heart rate HR of the patient P1, which is extracted from cyclical fluctuations in light reflection off the facial skin;
- Perspiration, which is extracted from cumulative light reflection of the skin;
- Degree of eye opening, which is extracted using facial recognition software;
- Dilation of pupils, which is extracted using facial recognition and/or pupil tracking software;
- Steady versus wandering focus, which is extracted using pupil tracking software;
- Posture P, which is extracted by analyzing changes in sitting position relative to a reference body outline that can be calibrated for the patient;
- Facial expression F according to number and length of wrinkle lines in the face, which can be extracted using pattern recognition software;
- Emotional content in the voice according to tonality and patterns of speech, which can be assessed using voice analysis software;
- Breathing (for example heavy breathing), extracted by analyzing the video stream and/or an audio signal generated by the patient and recorded by the second device.

Particularly, the physician's/clinician's web interface provided via the first device 2 associated to the physician/clinician displays (e.g. on display 20) in real-time the quantitative assessment of each of the pain-related parameters from the video stream S1. The physician/clinician P2 has the option of viewing each individual assessment, or the method/software can calculate a composite score of pain level based on weighted combination of each of the individual assessments.

In the case of remote control of the stimulation by the medical device 4, the method/software can maintain a running log of the stimulation parameters used and particularly calculates pain score with each parameter set. The history of parameter sets and composite pain scores can be reviewed. Alternatively, in the case that the physician/clinician P2 walks the patient P1 through the stimulation parameter changes, the clinician can manually input the stimulation parameters and markers in time to record when the patient P1 changes the active stimulation. In this case, voice recognition software may be used to extract parameter sets from the physician's/clinician's verbal instructions for saving in the log.

Particularly, FIG. 1 shows that the patient's implantable medical device 4, here in the form of an implantable pulse generator (IPG), that has a programming and data link C with the second device 3 associated to the patient (e.g. patient remote control). Particularly, the patient remote control 3 is used to capture a sequence of optical images S1 of the patient (i.e. a video stream) P1 and an audio signal S2 of the patient P1, wherein the second device 3 sends the data (e.g. video stream and audio signal) S1, S2 (particularly after pre-processing) to the remote first device 2 associated to the physician/clinician P2 (e.g. via an internet connection). The first device 2 can be a computing device such as a workstation. Meanwhile, in an embodiment, the video stream S1 and the audio signal S2 can also be captured at the first device 2 and sent to the second device 3 (e.g. patient remote control) for the patient P1 to see and hear. The first device 2 may also send program information down to the second device 3, which then sends the programming to the medical device (here IPG) 4, e.g. for changing stimulation parameters of the neurostimulation of the patient (e.g. spinal cord stimulation). The first device 2 can perform a video analysis and can display information for the medical personal P2 (e.g. physician/clinician etc.), which is detailed further below.

Figure 2:
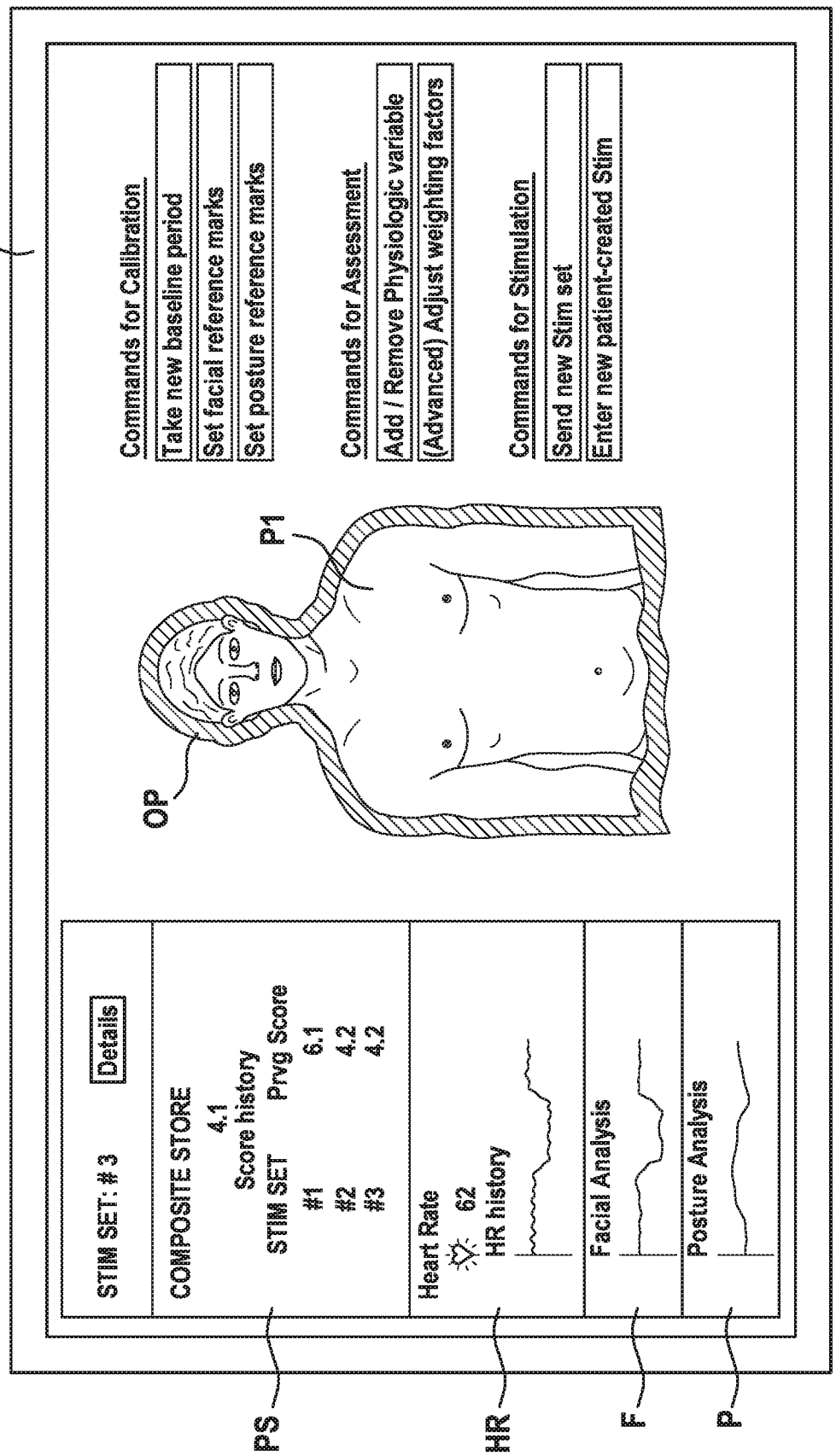
FIG. 2 shows an embodiment of a first device, particularly an interface design of the first device associated to the technical user (e.g. physician/clinician)

FIG. 2 shows an example of a software interface (e.g. implemented on the first device 2 and displayed on display 20) for the technical user (e.g. physician/clinician) P2 who is performing the assessment and potential re-programming. As shown, the technical user P2 is able to view details about the presently delivered stimulation parameter set. The technical user P2 can see in real time the present composite pain score PS and a history of average composite pain scores obtained during previous stimulation set tests. The technical user P2 can see the individual physiologic parameters that are used in calculating the pain score; in this case, the parameters are heart rate HR, facial expression F (e.g. derived from length and/or number of wrinkles of the facial skin of the patient P1), and posture P. The technical user P2 is able to view a historical trend of these variables HR, F, P that gets updated in real time. This allows the technical user P2 to incorporate his own judgement into interpretation of the data in addition to looking at the composite pain score PS outputs.

As shown further in the center of FIG. 2, the technical user P2 is able to view the patient P1 video stream S1 in real time. Particularly, the software/method provides reference guides to aid in aligning the patient face and/or body to an outline OP1 such that the analysis tools can function optimally.

As further illustrated in the right hand side of FIG. 2, the technical user P2 may have functions available that can be used for calibrating the setup prior to evaluating stimulation parameter sets. Prior to running a stimulation test, a baseline assessment period can be used to collect reference data for the individual patient. This reference can be used as a basis for comparison of the physiological parameters when each stimulation is delivered. In one embodiment, an absolute pain score can be entered according to patient feedback for this baseline period. This absolute value of manually-entered pain score can be used as a calibration for reporting all assessed pain levels relative to the starting pain score. Calibration setup also includes the ability to identify reference markings on the face or body of the patient to optionally aid with facial or posture analysis processing.

Furthermore, as shown in FIG. 2, the technical user can have options to customize the assessment. Particularly, the user can choose which physiological parameters are displayed on the screen 20 of the first device 2 for manual interpretation. The user P2 can also adjust the factors and weighting of factors that are used in calculating the composite pain score PS.

Finally, in a further embodiment, integrated into the same interface of the first device 2 shown in FIG. 2, the technical user P2 is able to create and send a new stimulation parameter set to the patient P1 (e.g. via the second device 3) in order to actively control the stimulation being delivered. Alternatively, if the patient makes manual adjustments to ongoing stimulation, the technical user can enter a marker and/or record details of the patient-controlled stimulation set.

Figure 3:
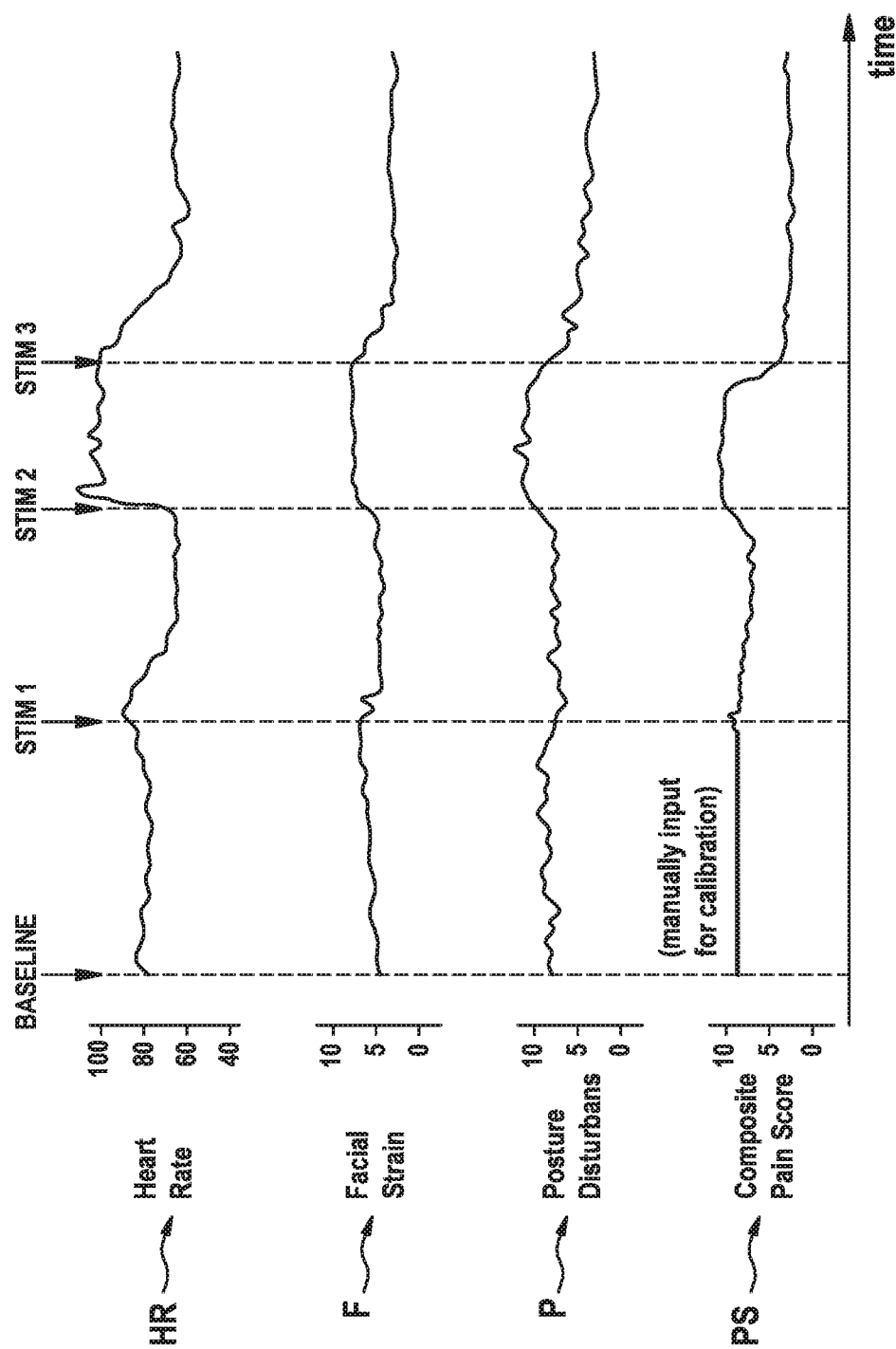
FIG. 3 shows an example of physiological parameters and composite pain score changes over time with stimulation.

FIG. 3 shows an example of physiologic parameter tracking and the resulting composite pain score over time. In this example, the parameters shown are: heart rate HR, facial strain F, and posture disturbance P. An increased pain level results in an increase in facial strain F (e.g. when the patient furrows the brow) and characteristic posture disturbances (e.g. hunch over of the patient's body). The tracking has a baseline data collection period that is used to serve as a reference before any stimulation is delivered. During this baseline period, a pain score can be manually recorded in order to report composite pain scores relative to this patient-provided rating. The method/software records when in time each stimulation set is started. In the example shown, the physiological parameters are indicating a reduction in pain during a first stimulation, an increase in pain during a second stimulation, and a further reduction in pain during a third stimulation.

According to an embodiment, facial strain F is a score calculated based on the analysis of the facial expression. Facial strain is quantified by the increase in wrinkles around the eyes, forehead, and/or mouth and nose relative to baseline facial expression.

According to an aspect, posture disturbance P is a score calculated based on analysis of the posture. Posture disturbance is calculated based on the deviation from a baseline resting posture. For example, the patient may hunch over more, raise up the shoulders, or sit more erectly compared to baseline.

Particularly, according to an embodiment, the composite pain score PS is derived from calculating a change in pain Δpain that is the sum of the weighted changes in physiological parameters. As an example, the change in pain Δpain can be calculated as $$\Delta pain = a\Delta HR + b\Delta F + c\Delta P = a(HR_f - HR_i) + b(F_f - F_i) + c(P_f - P_i)$$

i.e., the change in pain Δpain is the sum of a change in heart rate HR multiplied by a constant a, a change in facial strain F multiplied by a constant b, and a change in posture disturbance P multiplied by a constant c. Here, particularly, $HR_i$, $F_i$, $P_i$ are the initial values whereas $HR_f$, $F_f$, $P_f$ are the final values, e.g. after alteration of stimulation settings.

The calculated difference between the reference value and the actual value represents the degree of change of facial strain F and posture disturbance P.

The change in pain can then be added to the baseline pain score in order to report a composite pain score PS according to the physiological parameter assessment at any given point in time.

The present invention allows using video conferencing with quantitative assessment of pain levels with optional remote programming of a medical device that is e.g. used for neurostimulation, particularly spinal cord stimulation. Particularly, video communication is used as an alternative to the physical office visit, and multiple aspects of image analysis are used to quantitatively assess pain level fluctuations with different stimulation parameter settings.

Thus, the present invention particularly reduces the need for in-office follow-ups of neurostimulation (e.g. spinal cord stimulation), which leads to greater efficiency for the clinician and increased satisfaction for the patient. The incorporation of objective, quantitative measures of pain associated with different stimulation parameters helps to make more evidence-based selection of stimulation parameters to improve patient outcomes

The invention claimed is:

1. A system (1) for remote assessment of a patient (P1), comprising:
   a first device (2) associated to a physician (P2),
   a second device (3) associated to the patient (P1), wherein the second device (3) comprises or is connected to a camera (30) that is configured to acquire an optical image or a sequence of optical images (S1) of at least a portion of the patient (P1),
   a medical device (4) associated to the patient (P1), wherein the second device (3) is configured to communicate with the medical device (4), and wherein the medical device (4) is configured to be programmed via the second device (3),
   wherein the first device (2) is further configured to communicate with the second device (3) and/or with a service center, and wherein the second device (3) is configured to be at least temporarily controlled via the first device (2),
   wherein the second device (3) is configured to acquire data (S1, S2) indicative of at least one physiological parameter or of several physiological parameters (HR, F, P) of the patient (P1), wherein said data comprises the optical image or the sequence of optical images (S1), and
   wherein the first device (2) and/or the second device (3) and/or the external server is configured to analyze said optical image or sequence of optical images (S1) to determine at least one or several of the following physiological parameters: a perspiration of the patient (P1); a degree of eye opening of the patient (P1); a dilation of the pupils of the patient (P1); a state of a focus of the eyes of the patient (P1); a posture (P) of the patient (P1); the number and/or length of wrinkle lines of the face of the patient (P1) or a quantity derived therefrom,
   wherein the first device (2) and/or the second device (3) and/or the external server is configured to calculate a score (PS, Δpain) using said at least one physiological parameter or said several physiological parameters (HR, F, P), and
   wherein a baseline pain score is used as a calibration for reporting all assessed pain levels relative to the baseline pain score.

2. The system according to claim 1, wherein said data further comprises an audio signal (S2) generated by the patient (P1), wherein the second device (3) associated to the patient (P1) comprises or is connected to a microphone (31) that is configured to acquire said audio signal (S2).

3. The system according to claim 2, wherein the first device (2) and/or the second device (3) and/or the external server is configured to analyze said audio signal (S2) to determine at least one or several of the following physiological parameters: a tonality and/or pattern of speech of the patient (P1); a breathing rate of the patient (P1).

4. The system according to claim 2, wherein the first device (2), and/or the second device (3) and/or the external server, or a combination thereof, is configured to analyze a signal comprising said optical image or said sequence of optical images (S1) and said audio signal (S2) to determine physiological data.

5. The system according to claim 1, wherein the medical device (4) is an implantable medical device that is configured to be implanted into the patient (P1).

6. The system according to claim 1, wherein the medical device (4) is configured for neurostimulation of the patient (P1).

7. The system according to claim 1, wherein calculation of the score (PS, Δpain) comprises calculation of a weighted sum.

8. The system according to claim 1, wherein said score (PS, Δpain) is a measure for a physiological state of the patient (P1).

9. A method for remote assessment of a patient (P1) using a system (1) according to any one of the preceding claims, wherein data (S1, S2) indicative of at least one physiological parameter (HR, F, P) or of several physiological parameters of the patient (P1) is acquired by the second device (3), wherein said data comprises an optical image or a sequence of optical images (S1) of at least a portion of the patient (P1), and wherein the optical image or the sequence of optical images (S1) is analyzed by the first device (2) and/or the second device (3) and/or the external server so as to determine at least one or several of the following physiological parameters: a perspiration of the patient (P1); a degree of eye opening of the patient (P1); a dilation of the pupils of the patient (P1); a state of a focus of the eyes of the patient (P1); a posture (P) of the patient (P1); the number and/or length of wrinkle lines of the face of the patient (P1) or a quantity derived therefrom;

wherein a score (PS, Δpain) is calculated using said at least one parameter or said several parameters (HR, F, P) by means of the first device (2) and/or the second device (3) and/or the external server.

10. The method according to claim 9, wherein said data further comprises an audio signal (S2) generated by the patient (P2).

11. The method according to claim 10, wherein said audio signal (S2) is analyzed by the first device (2) and/or the second device (3) and/or the external server so as to determine at least one or several of the following physiological parameters: a tonality and/or pattern of speech of the patient (P1); a breathing rate of the patient (P1).

12. The method according to claim 9, wherein particularly said score (PS, Δpain) is a measure for a physiological state of the patient (P1).

13. The system according to claim 3, wherein the tonality and/or pattern of speech of the patient (P1) is an emotional content in the voice of the patient (P1).

14. The system according to claim 3, wherein the first device (2) and/or the second device (3) and/or the external server is configured to determine the tonality and/or pattern using a voice analyzing algorithm carried out by the first device.

15. The system according to claim 1, wherein the second device is formed as a mobile phone or a smart phone.

* * * * *